(12) United States Patent
Seex

(10) Patent No.: US 11,944,323 B2
(45) Date of Patent: Apr. 2, 2024

(54) SURGICAL TOOL

(71) Applicant: Kevin Seex, Kingswood (AU)

(72) Inventor: Kevin Seex, Kingswood (AU)

(73) Assignee: RETROSPINE PTY LTD, Sydney (AU)

( * ) Notice: Subject to any disclaimer, the term of this patent is extended or adjusted under 35 U.S.C. 154(b) by 360 days.

(21) Appl. No.: 16/673,763

(22) Filed: Nov. 4, 2019

(65) Prior Publication Data

US 2020/0138455 A1  May 7, 2020

Related U.S. Application Data

(63) Continuation of application No. 14/650,424, filed as application No. PCT/AU2013/001425 on Dec. 18, 2013, now abandoned.

(30) Foreign Application Priority Data

Dec. 8, 2012  (AU) .................................. 2012905345

(51) Int. Cl.
*A61B 17/16* (2006.01)
*A61B 17/00* (2006.01)
(Continued)

(52) U.S. Cl.
CPC ...... *A61B 17/1659* (2013.01); *A61B 17/1671* (2013.01); *A61B 17/7074* (2013.01);
(Continued)

(58) Field of Classification Search
CPC .... A61F 2/4684; A61F 2/4603; A61F 2/4611; A61B 17/1659; A61B 17/1671;
(Continued)

(56) References Cited

U.S. PATENT DOCUMENTS 5,531,749 A   7/1996  Michelson
5,569,298 A   10/1996 Schnell
(Continued)

FOREIGN PATENT DOCUMENTS

CN   104771251   7/2015
EP   1391189    4/2008
(Continued)

OTHER PUBLICATIONS

PCT International Search Report, PCT/AU2013/001425 dated Feb. 10, 2014. pp. 1-4.
(Continued)

*Primary Examiner* — Marcela I. Shirsat
(74) *Attorney, Agent, or Firm* — MORRISS O'BRYANT COMPAGNI CANNON, PLLC

(57) ABSTRACT

A surgical tool for use in gaining access to the spine and including a part which is arranged to avoid other anatomical structures when the tool is in use; the tool comprising: a distal working end formation, a proximal end and intermediate said ends a formation displaced from a longitudinal axis and extending between said distal and proximal ends wherein the displaced formation is arranged to avoid said other anatomical structures anatomy during use of the working end of the tool.

10 Claims, 18 Drawing Sheets

(51) Int. Cl.
*A61B 17/70* (2006.01)
*A61B 90/00* (2016.01)
*A61F 2/44* (2006.01)
*A61F 2/46* (2006.01)

(52) U.S. Cl.
CPC .............. *A61F 2/44* (2013.01); *A61F 2/4684* (2013.01); *A61B 2017/00464* (2013.01); *A61B 17/7092* (2013.01); *A61B 2090/062* (2016.02); *A61F 2/4611* (2013.01)

(58) Field of Classification Search
CPC ............ A61B 17/7074; A61B 17/7092; A61B 2017/0046; A61B 2017/00464
USPC ............................................ 623/17.11–17.16
See application file for complete search history.

(56) References Cited

U.S. PATENT DOCUMENTS

| | | |
|---|---|---|
| 6,423,073 B2 * | 7/2002 | Bowman ............ A61B 17/0401 606/88 |
| 6,425,920 B1 | 7/2002 | Hamada |
| 7,135,043 B2 | 11/2006 | Nakahara et al. |
| 7,232,463 B2 | 6/2007 | Falahee |
| 7,862,593 B2 | 1/2011 | Clement et al. |
| 8,016,829 B2 | 9/2011 | Mahoney et al. |
| 8,083,778 B2 | 12/2011 | Clement et al. |
| 8,088,163 B1 | 1/2012 | Kleiner |
| 8,114,139 B2 | 2/2012 | Sournac et al. |
| D656,610 S | 3/2012 | Kleiner |
| 8,277,510 B2 | 10/2012 | Kleiner |
| 8,292,960 B2 | 10/2012 | Kleiner |
| 8,366,748 B2 | 2/2013 | Kleiner |
| 8,419,795 B2 | 4/2013 | Sweeney |
| 8,506,632 B2 | 8/2013 | Ganem et al. |
| 8,506,636 B2 | 8/2013 | Dye |
| 8,715,355 B2 | 5/2014 | Kleiner |
| 8,801,786 B2 | 8/2014 | Bernard et al. |
| 8,808,305 B2 | 8/2014 | Kleiner |
| 8,840,620 B2 | 9/2014 | Recoules-Arche et al. |
| 8,840,666 B2 | 9/2014 | Crozet |
| 8,845,733 B2 | 9/2014 | O'Neil et al. |
| 8,852,278 B2 | 10/2014 | Bellas |
| 8,864,764 B2 | 10/2014 | Groiso |
| 9,078,706 B2 | 7/2015 | Kirschman |
| 9,101,492 B2 | 8/2015 | Mangione et al. |
| 9,119,729 B2 | 9/2015 | Falahee |
| 9,180,024 B2 | 11/2015 | Mahoney et al. |
| 9,186,193 B2 | 11/2015 | Kleiner et al. |
| 9,216,096 B2 | 12/2015 | Lynn et al. |
| 2002/0147460 A1 | 10/2002 | Bacher |
| 2002/0165550 A1 * | 11/2002 | Frey ................... A61B 17/1671 606/85 |
| 2003/0139812 A1 | 7/2003 | Garcia et al. |
| 2006/0276816 A1 | 12/2006 | Eckman |
| 2007/0100339 A1 | 5/2007 | Clement et al. |
| 2007/0276406 A1 | 11/2007 | Mahoney et al. |
| 2007/0293949 A1 | 12/2007 | Salerni et al. |
| 2008/0097454 A1 | 4/2008 | DeRidder et al. |
| 2009/0082811 A1 | 3/2009 | Stad et al. |
| 2009/0209998 A1 | 8/2009 | Widmann |
| 2010/0082030 A1 | 4/2010 | Groiso |
| 2010/0087822 A1 | 4/2010 | Groiso |
| 2011/0004222 A1 | 1/2011 | Biedermann et al. |
| 2011/0015679 A1 | 1/2011 | Fiere et al. |
| 2011/0087074 A1 * | 4/2011 | Hardenbrook ..... A61B 17/0218 600/210 |
| 2011/0112580 A1 | 5/2011 | Clement et al. |
| 2011/0112581 A1 | 5/2011 | Clement |
| 2011/0118842 A1 | 5/2011 | Bernard et al. |
| 2011/0172769 A1 | 7/2011 | Ganem et al. |
| 2011/0202096 A1 | 8/2011 | White et al. |
| 2011/0276139 A1 | 11/2011 | Mahoney et al. |
| 2012/0004684 A1 | 1/2012 | Reinauer |
| 2012/0116512 A1 | 5/2012 | Sournac et al. |
| 2012/0201322 A1 | 8/2012 | Rakib et al. |
| 2012/0226358 A1 | 9/2012 | Kleiner |
| 2012/0277867 A1 | 11/2012 | Kana et al. |
| 2013/0053967 A1 | 2/2013 | Sournac et al. |
| 2013/0096684 A1 | 4/2013 | Kleiner |
| 2013/0150898 A1 | 6/2013 | Wong et al. |
| 2013/0184825 A1 | 7/2013 | Kleiner |
| 2013/0211524 A1 | 8/2013 | Hugues |
| 2014/0172105 A1 | 6/2014 | Frasier et al. |
| 2015/0025640 A1 | 1/2015 | Malandain |
| 2015/0297247 A1 | 10/2015 | Seex |
| 2016/0022434 A1 | 1/2016 | Robinson |
| 2016/0030029 A1 | 2/2016 | Mahoney et al. |
| 2016/0030190 A1 | 2/2016 | Robinson |

FOREIGN PATENT DOCUMENTS

| | | |
|---|---|---|
| FR | 2816201 | 5/2002 |
| JP | 2007521886 | 8/2007 |
| TW | 201036587 | 10/2010 |
| TW | 201125533 | 8/2011 |
| WO | WO9529641 | 11/1995 |
| WO | WO0238086 | 5/2002 |
| WO | WO2005077288 | 8/2005 |
| WO | WO2006042335 | 4/2006 |
| WO | WO2010010522 | 1/2010 |
| WO | WO2011013047 | 2/2011 |
| WO | WO2014085870 | 6/2014 |

OTHER PUBLICATIONS

PCT Written Opinion of the International Searching Authority, PCT/AU2013/001425, dated Feb. 10, 2014. pp. 1-5.

* cited by examiner

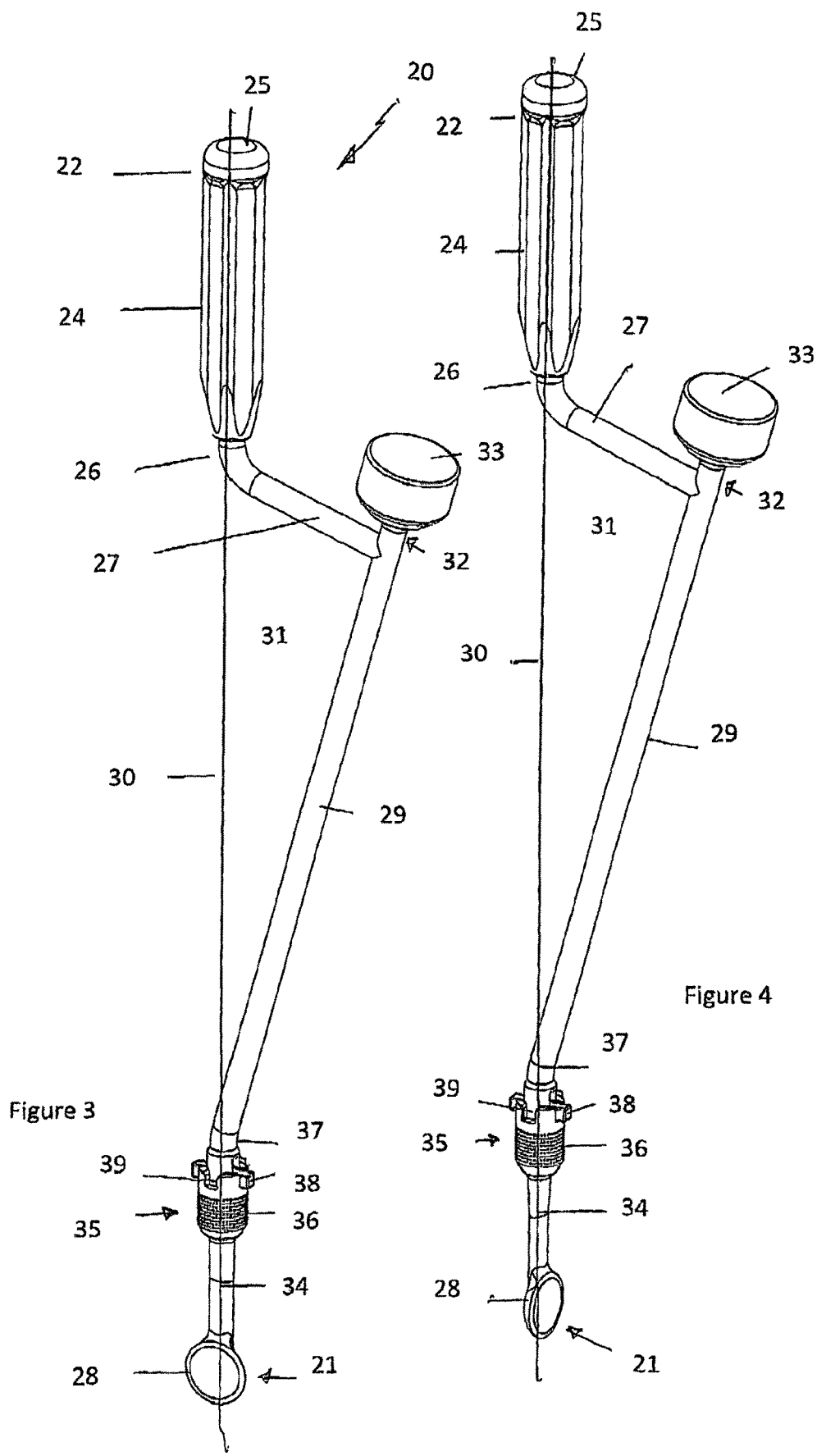

SURGICAL TOOL

CROSS-REFERENCE TO RELATED APPLICATIONS

This application is a continuation of co-pending U.S. patent application Ser. No. 14/650,424, filed Jun. 8, 2015, entitled SURGICAL TOOL which is a national stage application (under 35 U.S.C. § 371) of PCT/AU2013/001425 filed Dec. 8, 2013, published as WO 2014/085870 both of which are hereby incorporated by reference herein in their entirety, including but not limited to those portions that specifically appear hereinafter, the incorporation by reference being made with the following exception: In the event that any portion of the above-referenced application is inconsistent with this application, this application supercedes said above-referenced application.

BACKGROUND

The present invention relates to surgical tools and appliances and more particularly, relates to a tool for use in spinal surgery. More particularly the invention relates to a tool which is capable of avoiding anatomy in one area while accessing anatomy in another area of the human body. The invention further relates to a tool having an offset region between a holding end and a working end, the offset region enabling avoidance of anatomy at or near the offset region and encountered along a path between the holding end and working end. The invention further relates to surgical tools for use in particular though not exclusively in spinal surgery where skin incision and surgical approach through soft tissue is not the desired line of approach required for the working end of tools and implants used with the tool.

PRIOR ART

Various manual surgical tools have been described in the prior art for use in a variety of surgical procedures. Examples of known surgical tools generally having a holding end and a working end are described in the following patent specifications which are incorporated by reference herein, US2012201322, TW 201036587, TW201125533, US2002147460, US2009209998, US2011202096, US2012004684 and WO9529641.

One of the problems in surgery is gaining suitable access to the anatomical site on which surgery is to be performed but at the same time avoiding damage to surrounding tissues and anatomy in gaining access to that site, Tools used to gain access to a site can cause unwanted collateral damage to surrounding structures by such events as bruising, constricting of muscles, nerves and vessels. One objective is to perform surgery with little or no damage to surrounding tissues and structures so that the patient's pain is minimised and recovery time kept to a minimum.

Typically a surgical instrument generally has three parts, a handle, shaft and a working end. Typical straight instrument have handle shaft and working end in same plane and along a longitudinal axis, Numerous instruments are known which have distal working ends that are curved or angled relative to the shaft and handle. Some instruments have distal working ends whose angle can be adjusted as required. Bayonet shaped instruments are known in neurosurgery that place a handle out of a long axis of instrument to improve line of sight. Also known are instruments with rotating shafts, rotating distal working ends or rotating handles. There are a type of instrument known as retractors, which have a distal blade portion to engage tissues. Parts of these instruments e.g. blades, shafts or handles may be shaped to allow retraction beneath the edge of a wound or through an opening of a body orifice. Thus they are shaped to avoid anatomical structures but the handle is used for gripping and is not used to indicate the alignment or position of the distal blade.

Instruments are also known that allow approach and work on a spinal disc space from an anatomically superior position. These instruments have a single distal angle to allow work on the disc when the incision is not aligned with the disc space. In these instruments the longitudinal axis of the handle is not in the same longitudinal axis as the distal working end. Monitoring the correct angle of the distal end to prevent endplate perforation is usually done using x-rays, There are several surgical approaches to the lumbar spine including disc spaces that are commonly used for fusion or disc replacement surgery. One approach to the disc space is via the side with the patient positioned laterally i.e. on their side.

The lateral approach to the spine is commonly employed. It is useful as an approach as it avoids anatomy that gets in the way when using other more common approaches e.g. posterior or anterior, There are a number of known commercially available lateral approach systems, for instance—XLIF from Nuvasive or DLIF from Medtronic. These approaches typically traverse the psoas muscle using Neuromonitoring to detect and thus avoid nerves which normally pass through this muscle.

In routine lateral approach surgery, the approach is at right angles to the long axis of the spine. The patient is positioned very carefully and secured, and then multiple xrays are used in order that instruments are kept orthogonal to the spine and in line with the disc space. It is dangerous if instruments move out of this line in case they injure important neighbouring structures. This is particularly important when crossing the disc space because the disc space is narrow and the distal edge of the instruments cannot be seen, thus its position has to be judged using a combination methods such as uniplanar xrays to assess depth combined with vertical handle position to confirm instruments remains parallel to disc space.

In routine lateral surgery at right angles to the spine, skin and soft tissue incisions are preferably made directly over and in line with the disc space e.g. at L34, 23 but often at L45 (and always at L5/s1) the bony pelvis prevents a true lateral approach to the disc space. At L112 and T12/L1 the ribs and diaphragm interfere in a similar way although instruments can be passed between ribs and through the diaphragm, but it would be desirable to avoid needing to traverse the diaphragm because of risk to the contents of the pleural cavity.

In lateral surgery to access the spine and the psoas muscle overlying it, the skin is incised directly lateral to the disc space and then the surgery passes through the muscles of the body wall, then though the retroperitoneal space allowing the peritoneum and its contents to fall anteriorly away from the approach. This creates a space corresponding anatomically to the retroperitoneum which extends inferiorly inside the bony pelvis upwards and under the ribs and beneath the diaphragm. In this type of surgery the nerves and spinal canal are generally not seen, but their position is predicted by knowledge of adjacent structures and X-rays. Typically, the surgeon can see the instrument entering the disc space but cannot see beyond this. Much of the work on the disc space is kept at right angle to the spine by assessing the position of the instrument handles. An assistant stands at the end of the bed and verifies the handle is correctly orientated to ensure the distal end is neither too far anterior or posterior. The depth of the instrument is judged by the surgeon with help from marks on the instruments and AP xrays.

When operating it is easier for a surgeon to remain orientated i.e. understand anatomy and relative position of critical structures e.g. vessels, spinal canal and nerve roots, if the spine is either flat or rotated at 90 degrees. This is also true for surgeons to understand the position of instruments relative to important structures particularly when the distal parts of the instruments cannot be seen. This is particularly important when placing implants or performing critical maneuvers e.g. contra lateral release of the disc space. In lateral systems the ability to work orthogonal to the spine over the L45 disc space varies with the individual patient because of degeneration or the shape of the spine or pelvis. This is recognized by some companies e.g in the Nuvasive XLIF instrumentation which has angled instruments which have a distal end which angle so that they can be used from a lateral approach from above the disc space when the anatomy is unfavourable for a true in line approach.

In these instruments with distal angled ends, the distal ends cannot be seen and their angle and depth has to be inferred from Xrays. Xrays are not always required to show depth because depth can be estimated by indicator marks on the visible part of instrument. As the handles of these instruments is parallel to the working end in one plane only, so the handle can only be used to guide position in one plane only, thus x-rays are thus required to show angle of instrument to avoid endplate injury.

Anterolateral/Oblique. An alternative approach to the lumbar spine is to employ the lateral position but rather than go through the psoas muscle which contains the lumbar plexus (nerves) and requires Neuromonitoring, the surgeon can approach the spine anterior to the psoas muscle retracting psoas posteriorly. This is also known as the oblique approach. This approach does not require Neuromonitoring. This exposes the spine also through the retroperitoneal space, and remains lateral and posterior to large blood vessels. This approach is particularly useful at L45 and L5/S1 disc spaces as it avoids the bony pelvis. The incision is typically anterior to the bony pelvis and the muscles are split in the line of their fibres. The spine and disc spaces can be exposed, and work performed obliquely. This approach using conventional instruments means surgeons work at an angle at about 10-45 degree off vertical to the spine.

The advantage of this approach is that all of the lumbar discs (including L5/S1) can be approached anterio laterally avoiding the need to traverse psoas and the use of Neuromonitoring. The disadvantage to this approach is that the incision through the body wall is not true lateral and thus one has to be very careful using straight instruments to approach the spine in case they pass too far posteriorly injuring the posteriorly situated nerves.

In both lateral and anterolateral approaches there are some critical parts of the operation where a true lateral (90 degrees) approach to the disc space is preferred in order to ensure safe positioning of the distal end of instruments. Examples include disc removal, endplate preparation, disc space distraction, disc space release where the disc space is completely crossed in order to release the contralateral annulus, another example is implant trial and final implant positioning.

It would be an advantage but the prior art does not teach, angled instruments in which the distal working end of the instrument is angled to allow this end to be correctly aligned to the disc space, with the handle also providing visual confirmation of this positron with reference to a longitudinal axis passing through proximal and distal ends of the instrument.

INVENTION

With this in mine it is an advantage to be able to use instruments that pass through disc space at right angles to a long axis of the spine and in line with the disc space where not only is the distal working end of the instrument angled to allow that end to be correctly aligned to the disc space, but also that the handle provides visual confirmation of this position. The invention provides a surgical tool having an offset region between a holding end and a working end, the offset region arranged to enable avoidance of anatomy not involved in surgical treatment at or near the offset region. The invention further provides a surgical tool for use in gaining access to the spine while avoiding anatomical tissues and allowing an aligning relationship between a part of a proximal end of the tool and a distal working end of the tool.

According to one embodiment, the tool comprises a distal end, a proximal end and intermediate said ends a displaced region shaped to avoid anatomy during use of the tool. At a proximal end there is provided a gripping handle and the distal end includes a working formation. The displaced region between the handle and the working end is offset from a line which extends from the handle to the working end and defining a space in which anatomical structures will be present without obstructing the tool during use. According to one embodiment the handle and working end are substantially in alignment along a longitudinal axis.

In its broadest form the present invention comprises:
 a surgical tool for use in gaining access to the spine while avoiding anatomical tissues; the tool comprising a distal working end, a proximal gripping end and intermediate said ends a displaced region shaped to avoid anatomy during use of the tool.

In another broad form the present invention comprises:
 a surgical tool for use in gaining access to the spine and including a part which is arranged to avoid other anatomical structures when the tool is in use; the tool comprising:
 a distal working end formation, a proximal end and intermediate said ends a formation displaced from a longitudinal axis and extending between said distal and proximal ends wherein the displaced formation is arranged to avoid said other anatomical structures anatomy during use of the working end of the too.

Preferably the proximal end includes a gripping handle and the distal end includes a working formation which engages an anatomical structure. The displaced region between the handle and the working end is offset relative to a line between the handle and the working end and defines a space in which anatomical structures may be present during use of the tool. According to a preferred embodiment the handle and working end are co lineal in that they lie along a longitudinal axis. Forces applied at a proximal end, preferably via a gripping handle are transferred to the working end via the displaced region as if along a longitudinal axis.

According to a preferred embodiment, at least a part of the proximal end is in alignment with and has the same longitudinal axis as the distal end (i.e. the long axis through both ends points in same direction). The longitudinal axis passes through an intermediate region but the tool body is offset from the longitudinal axis at that intermediate region. The tool is preferably for use in a lateral and anterolateral approach to the spine, typically with the patient positioned in a lateral position. The purpose is to provide improved external control and improved visual indication of position of working end, when such position is not visible to the surgeon.

The present invention provides an alternative to the known prior art and the shortcomings identified. The foregoing and other objects and advantages will appear from the description to follow. In the description reference is made to the accompanying representations, which forms a part hereof, and in which is shown by way of illustration specific embodiments in which the invention may be practiced. These embodiments will be described in sufficient detail to enable those skilled in the art to practice the invention, and it is to be understood that other embodiments may be utilised and that structural changes may be made without departing from the scope of the invention. The following detailed description is, therefore, not to be taken in a limiting sense, and the scope of the present invention is best defined by the appended claims. It is a common feature in spinal surgical tools that their distal end frequently passes into the disc space and thus at least partly out of direct vision when a surgical line of sight is obscured by anatomy.

The present invention seeks to ameliorate or eliminate the attendant disadvantages which have been manifest in use of the prior art extraction tool assemblies by providing an improved tool which avoids unwanted contact with anatomy in a path between the gripping end and the working end.

BRIEF DESCRIPTION OF DRAWINGS

The present invention will now be described in more detail according to a preferred but non limiting embodiment and with reference to the accompanying illustrations wherein;

FIG. 3 shows an elevation view of a tool according to an alternative embodiment with a detachable working formation disposed in a first orientation.

FIG. 4 shows an elevation view of the tool of FIG. 3 with the detachable working formation disposed in a second orientation.

DETAILED DESCRIPTION

The present invention will now be described in more detail according to a preferred but non limiting embodiment. The examples referred to herein are illustrative and are not to be regarded as limiting the scope of the invention. While various embodiments of the invention have been described herein, it will be appreciated that these are capable of modification, and therefore the disclosures herein are not to be construed as limiting of the precise details set forth, but to avail such changes and alterations as fall within the purview of the description. Although the method and apparatus aspects of the invention will be described with reference to their application to sale of used and recycled hardware and building goods, it will be appreciated that the invention has alternative applications.

According to a preferred embodiment the tool has a variety of uses in spinal surgery. The invention will be described with respect to spinal surgery for multiple types of spinal instruments with the common feature that at least part of the distal working end has the same longitudinal axis as the longitudinal axis of at least part of a proximal end with those ends interposed with an intermediate section shaped to avoid anatomy there between. These instruments are designed for use in wounds where there is no line of sight between the long axis of the proximal and distal ends of the instrument.

Figure 1:
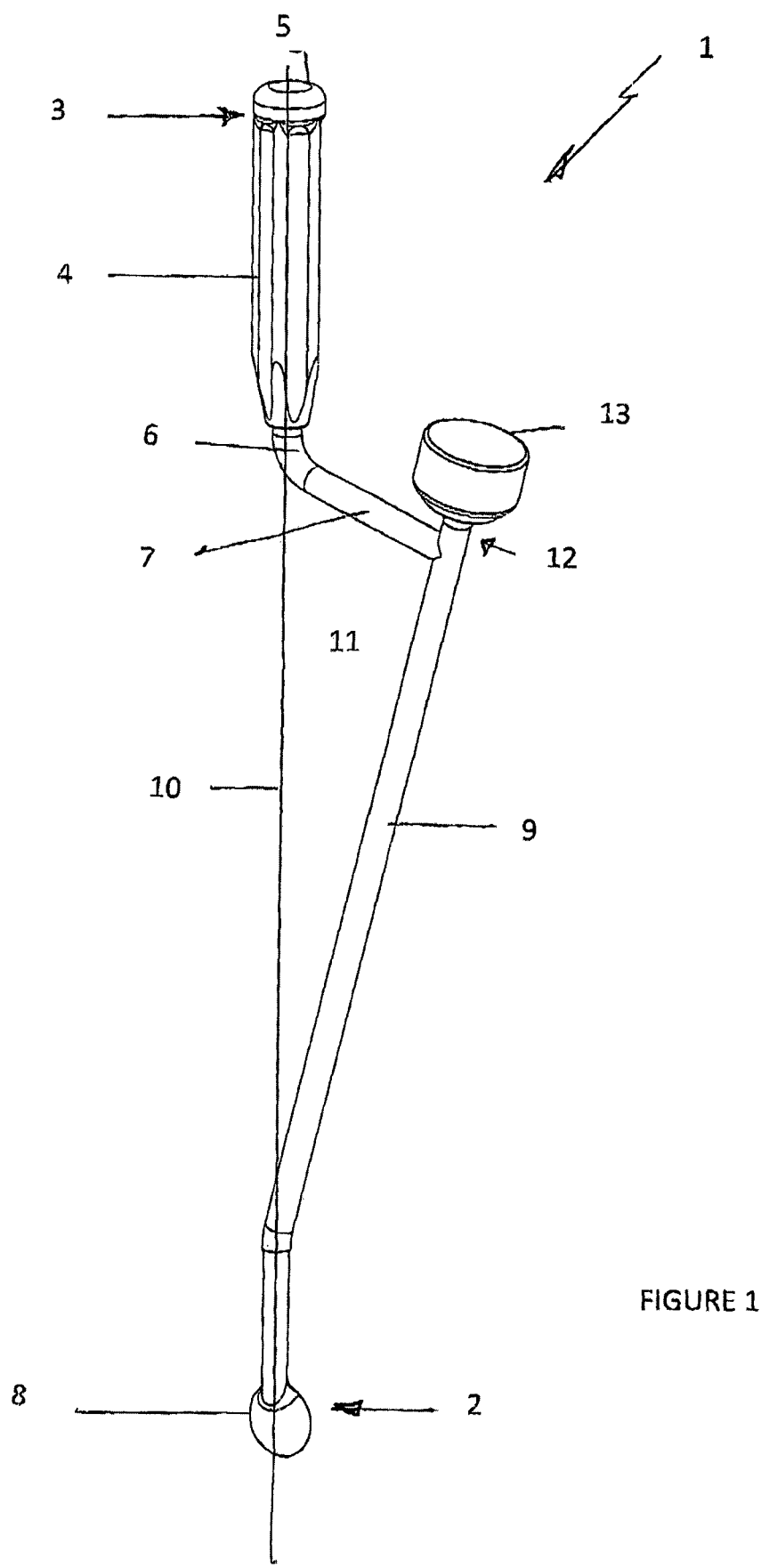
FIG. 1 shows an elevation view of a tool according to one embodiment including a working formation.

FIG. 1 shows an elevation view of a tool 1 according to one embodiment. Tool 1 comprises a distal end 2 and proximal end 3. Proximal end 3 comprises a gripping handle 4 having a free end 5 and terminating at end 6 in joining member 7. Distal end 2 includes a working formation 8. Intermediate working formation 8 and joining member 7 is arm 9 which transfers loads applied to the handle 4 to working formation 8. Tool 1 is characterized in that the handle 4 and working end formation 8 lie along the same longitudinal axis 10. Joining member 7 and arm 9 define a region 11 which is offset from the longitudinal axis 10. Region 11 is displaced from the longitudinal axis 10 so that tool 1 can be used to work on a surgical site but at the same time the intermediate displaced region 11 avoids unwanted contact with tissue which lies between the handle end 3 and the working end 2. Extending from end 12 of arm 9 is a platform 13 which can function as a bearing surface for additional applied load such as from a hammer.

Figure 2:
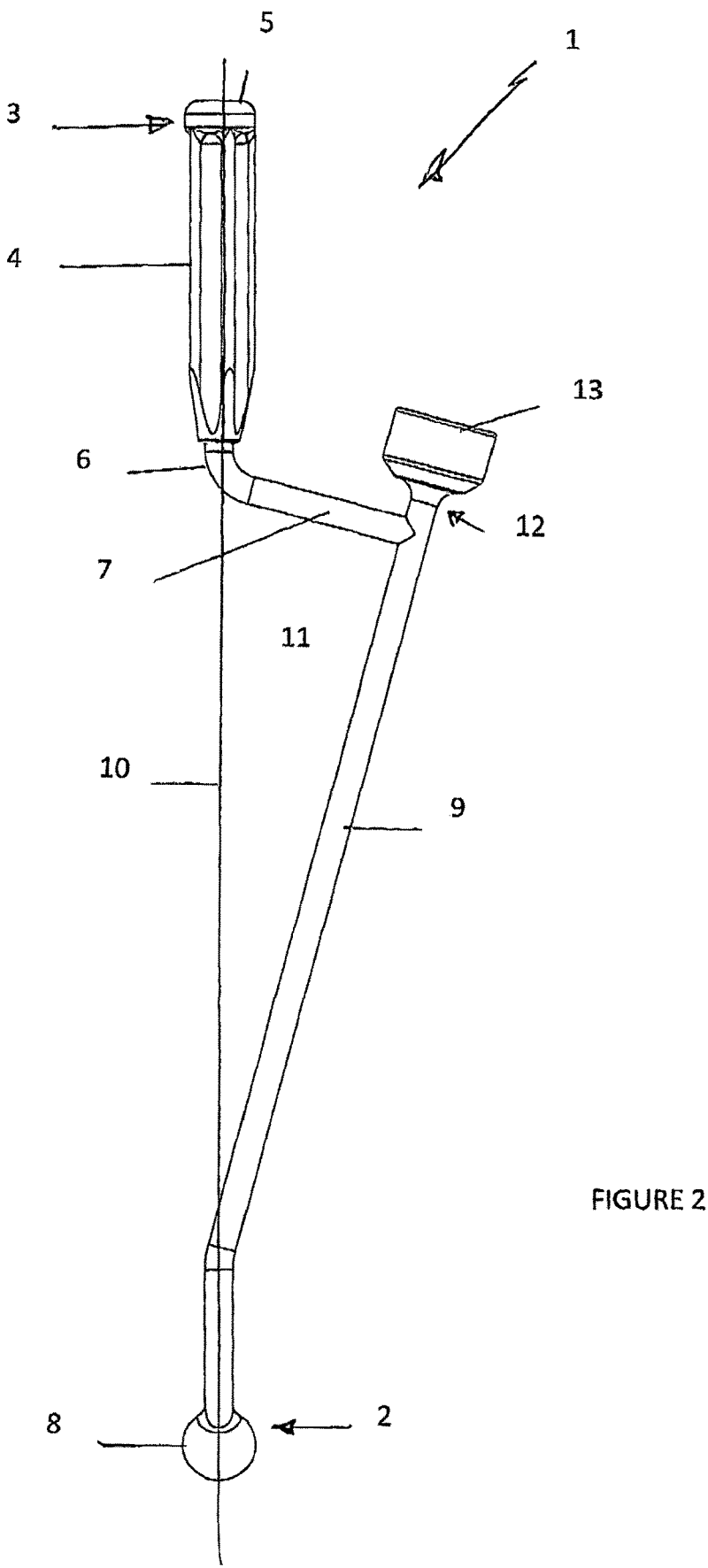
FIG. 2 shows an elevation view of the tool of FIG. 1 rotated about 45 degrees anticlockwise showing the working formation in an alternative orientation.

It will be appreciated according to one embodiment that the proximal end 3 functions as an indicator with the handle 4 located on joining member 7, Working formations 8 on the distal end 2 of the tool 1 may comprise Cobb elevator, rasp, curettes, distracters, trial implant and implant holder. Other working formations at the distal end 2 are contemplated depending upon the specific use of the tool 1. An advantage of the present invention is that the tool 1 can be held orthogonal to the longitudinal axis of a spine with the handle 4 indicating a path for the distal working end 2 and contributing to controlled movement of the distal end 2. The tool 1 is adapted with a displaced region 11 between the distal and proximal ends 2, 3 to avoid anatomical structures not involved in an operation. This means that the surgeon has the advantage that while the handle 4 and distal working end 2 are aligned orthogonal to the long axis of the spine and disc space the region 11 defined by joining arm 7 and arm member 9 to avoid anatomy. The proximal end handle 4 in addition to allowing control of the tool 1 acts as visual indicator of tool alignment so the surgeon, theatre assistants or staff can report if alignment is incorrect. The proximal handle 4 may be used to hold the tool for impaction or help guide the instrument while impaction forces are applied along a straight section of joining member and transferred to the working end formation 8. According to one embodiment the handle 4 or other proximal formation is adapted to receive a slap hammer for disc impaction. A further advantage of the tool 1 is that as the handle 4 is in line with the distal end 2 of the tool which allows surgeons to better judge the alignment of the distal end when it is not directly visible. FIG. 2 shows with corresponding numbering an elevation view of the tool of FIG. 1 rotated about 45 degrees anticlockwise showing the working formation in an alternative orientation.

FIG. 3 shows (an elevation view of a tool 20 according to an alternative embodiment. Tool 20 comprises a distal end 21 and proximal end 22. Proximal end 22 comprises a gripping handle 24 having a free end 25 and terminating at end 26 in joining member 27. Distal end 21 includes a detachable working formation 28 disposed in a first orientation. Intermediate working formation 28 and joining member 27 is arm 29 which transfers loads applied to the handle 24 to working formation 28. Tool 20 is characterized in that the handle 24 and working end formation 28 lie along the same longitudinal axis 30. Joining member 27 and arm 29 define a region 31 which is offset from the longitudinal axis 30. Region 31 is displaced from the longitudinal axis 30 so that tool 20 can be used to work on a surgical site but at the same time the intermediate displaced region 31 avoids unwanted contact with tissue which lies between the handle end 22 and the distal 21. Extending from end 32 of arm 29 is a platform 33 which can function as a bearing surface for additional applied load such as from a hammer. Working formation 28 is supported by arm 34. Arm 34 terminates in a connection assembly 35 comprising a sleeve 36 which engages co operating end formation 37 in male female inter fitting relationship. Key 38 engages slots 39 to provide a key in lock arrangement which prevents relative rotation of sleeve relative to end formation 37. In this arrangement the surgeon can select a variety of rotational positions for sleeve 36. This allows the surgeon to orient the working end formation 28 in a direction required for the particular surgery.

FIG. 4 shows with corresponding numbering an elevation view of the tool 20 of FIG. 3 rotated about 45 degrees anticlockwise showing the working formation 28 in an alternative orientation.

Figure 5:
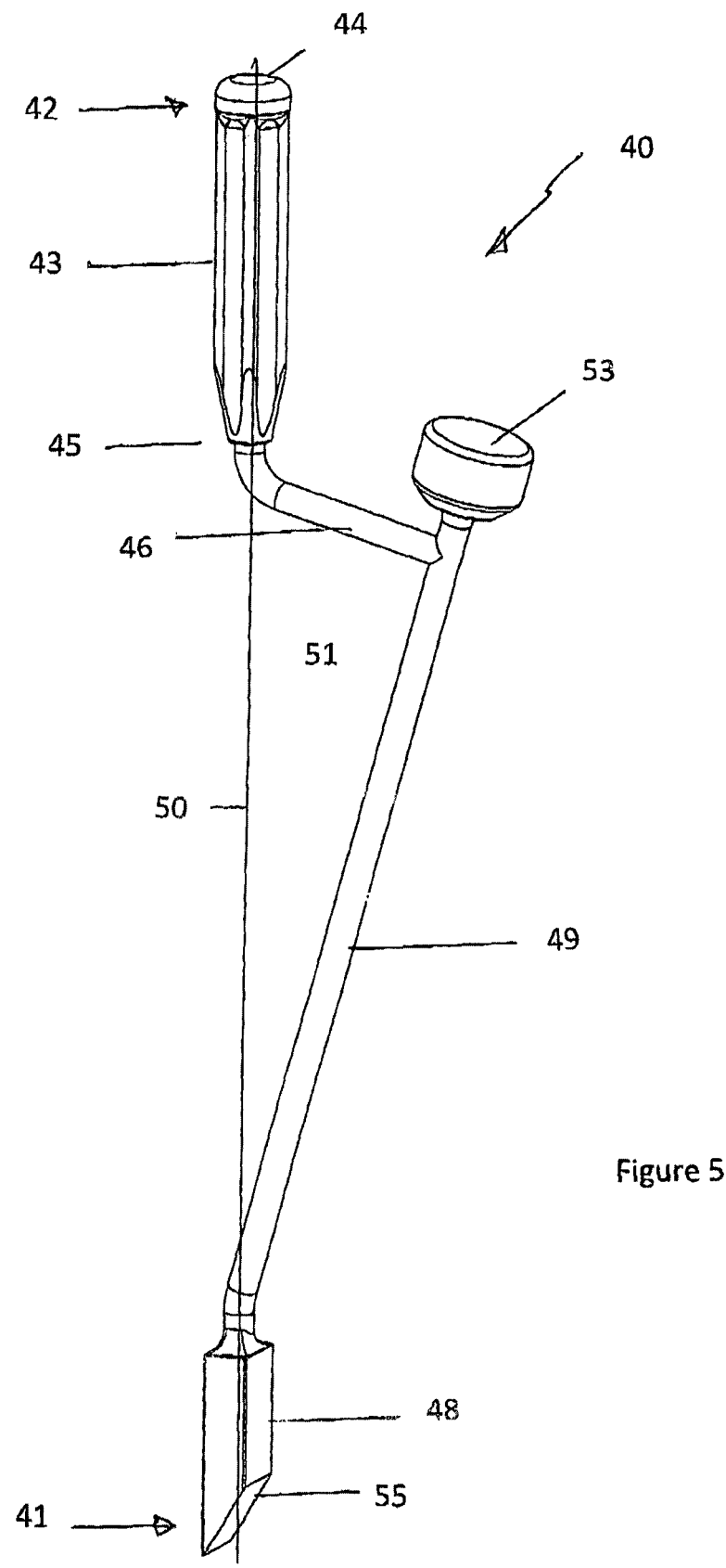
FIG. 5 shows an elevation view of a tool according to an alternative embodiment with a working formation disposed in a first orientation.
Figure 6:
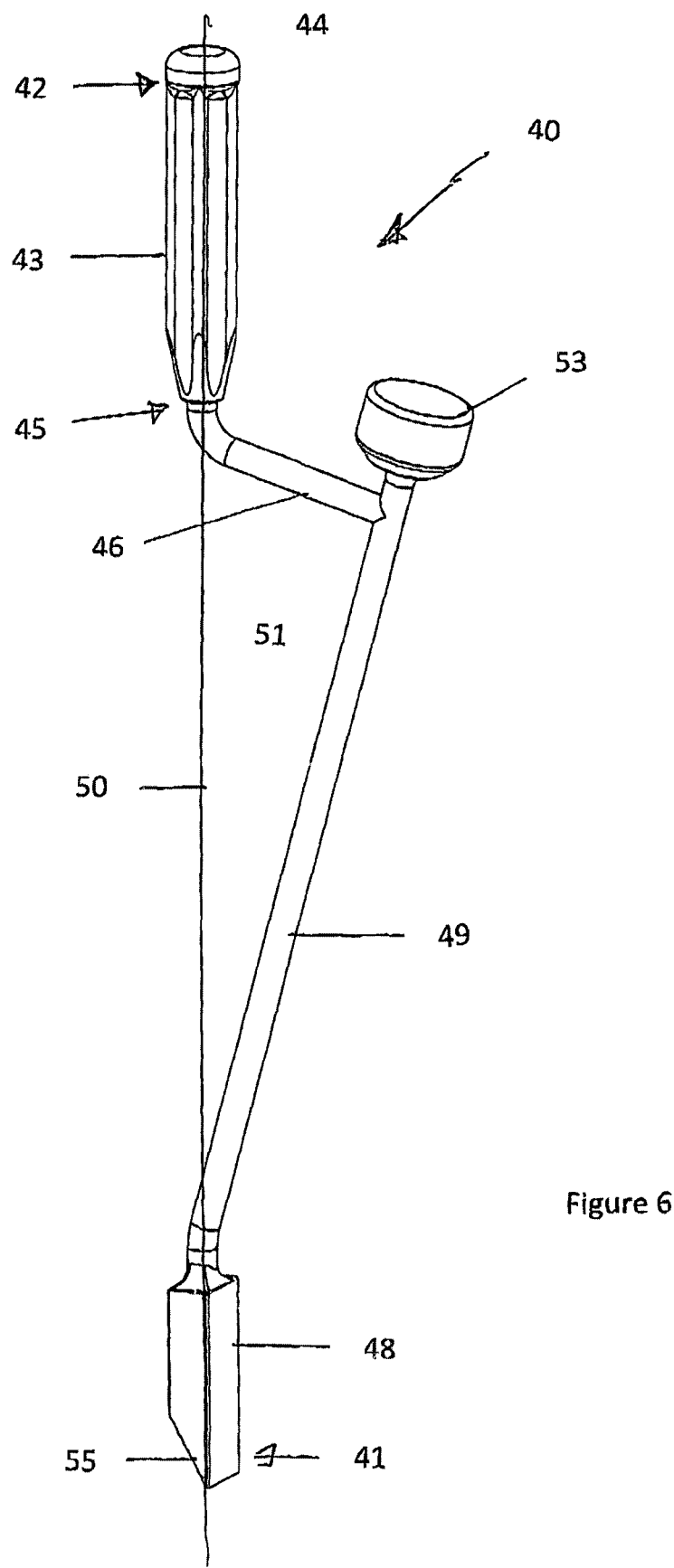
FIG. 6 shows an elevation view of the tool of FIG. 5 with the detachable working formation disposed in a second orientation.

FIG. 5 shows an elevation view of a tool 40 according to an alternative embodiment. Tool 40 comprises a distal end 41 and proximal end 42. Proximal end 42 comprises a gripping handle 43 having a free end 44 and terminating at end 45 in joining member 46. Distal end 41 includes a detachable working formation 48 disposed in a first orientation. Intermediate working formation 48 and joining member 46 is arm 49 which transfers loads applied to the handle 43 to working formation 48. Handle 43 and working end formation 48 lie along the same longitudinal axis 50. Joining member 46 and arm 49 define a region 51 which is offset from the longitudinal axis 50. Region 51 avoids unwanted instrument contact with tissue which lies between the handle end 42 and the distal end 41. Extending from end 42 of arm 49 is a platform 53 which can function as a bearing surface for additional applied load such as from a hammer. Working formation 48 is rotatably mounted via connection 54 to arm 49 and includes a distal end tapered region 55. This arrangement allows the surgeon to select a variety of positions for working formation 48. This allows the surgeon to orient the working end formation 48 in an orientation required for the particular surgery. FIG. 6 shows with corresponding numbering an elevation view of the tool of FIG. 5 with the detachable working formation 48 disposed in a second orientation.

Figure 7:
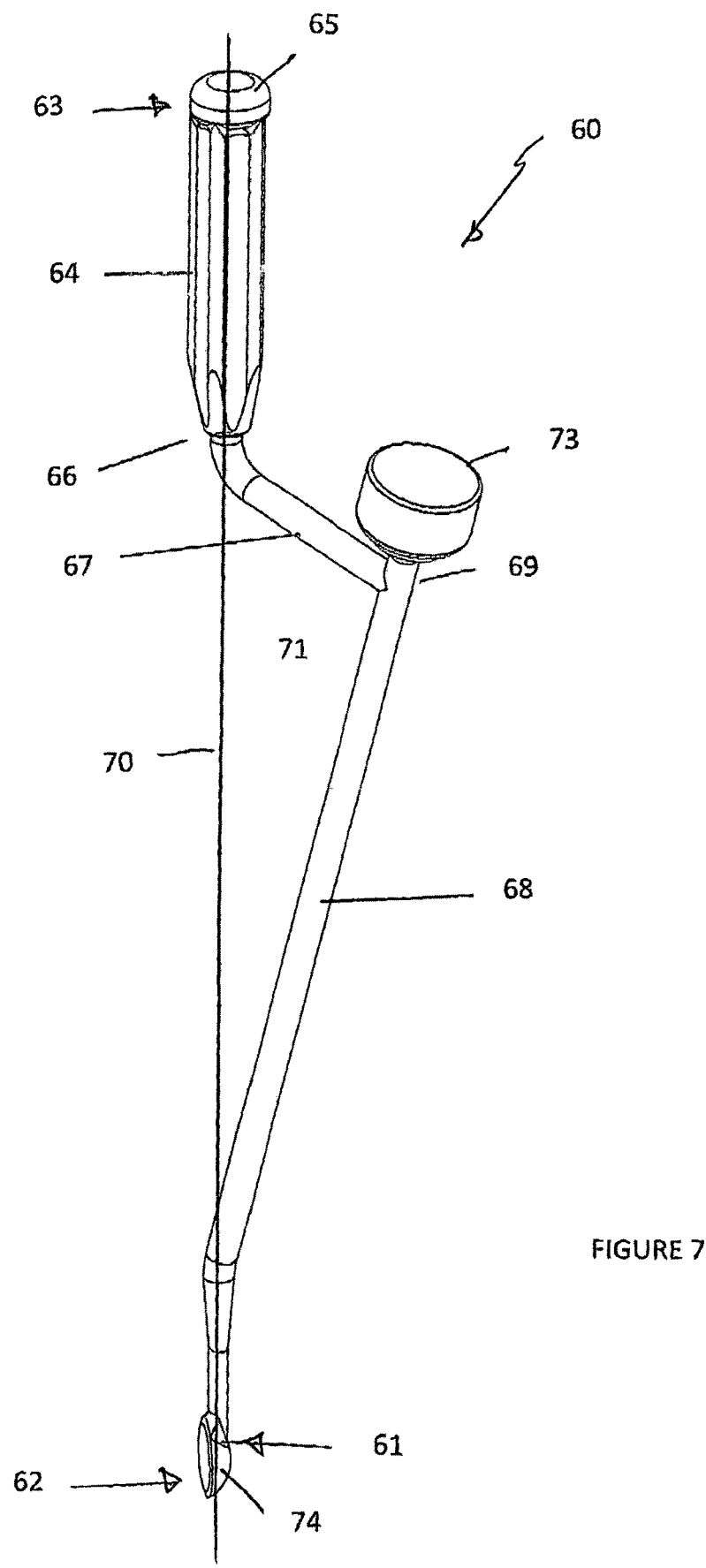
FIG. 7 shows an elevation view of a tool according to an alternative embodiment with an alternative working formation.
Figure 8:
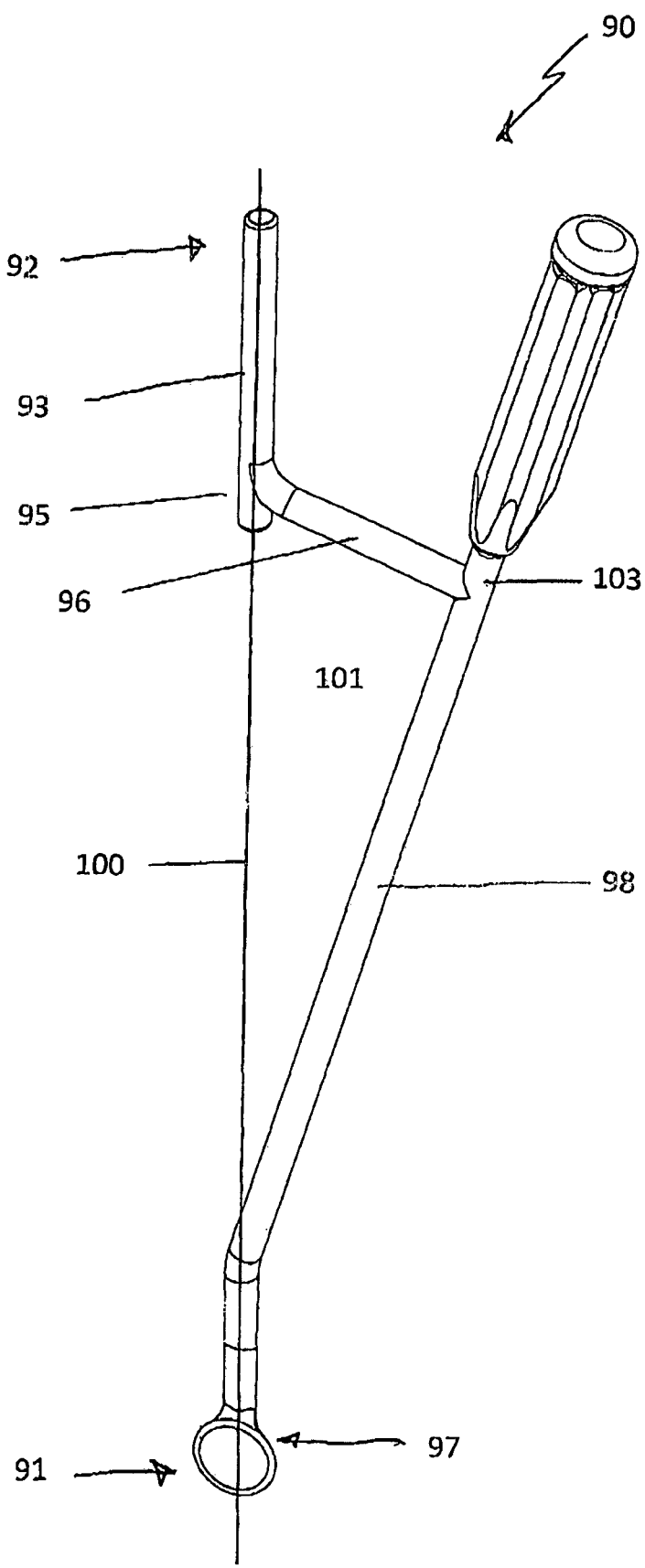
FIG. 8 shows an elevation view of a tool with a handle in an alternative location and a working formation.

FIG. 7 shows an elevation view of a tool 60 according to an alternative embodiment with an alternative working formation 61. Tool 60 functions in a similar manner to that described for the tool 40 of FIG. 5 save for the alternative working formation 61. Tool 60 comprises a distal end 62 and proximal end 63. Proximal end 63 comprises a gripping handle 64 having a free end 65 and terminating at end 66 in joining member 67. Distal end 62 includes a detachable working formation 61 disposed in a first orientation. Intermediate working formation 61 and joining member 67 is arm 68 which transfers loads applied to the handle 64 to working formation 61. Handle 64 and working end formation 61 lie along the same longitudinal axis 70. Joining member 67 and arm 68 define a region 71 which is offset from the longitudinal axis 70. Region 71 avoids unwanted instrument contact with tissue which lies between the handle end 63 and the distal end 62. Extending from end 72 of arm 68 is a platform 73 which can function as a bearing surface for additional applied load such as from a hammer, Working formation 61 depends from arm 69 and includes a distal cup 74. This allows the surgeon to use the working end cup 74 in an orientation and manner required for the particular surgery, FIG. 8 shows an elevation view of a tool 70 according to an alternative embodiment. Tool 90 comprises a distal end 91 and proximal end 92. Proximal end 92 comprises a post 93 having a free end 94 and terminating at end 95 in joining member 96. Distal end 91 includes a detachable working formation 97 disposed in a first orientation. Intermediate working formation 97 and joining member 96 is an arm 98 which transfers loads applied to the post 93 to working formation 97. Post 93 and working end formation 97 lie along the same longitudinal axis 100. Joining member 96 and arm 98 define a region 101 which is offset from the longitudinal axis 100. Region 101 as before avoids unwanted contact with soft and/or hard tissues which lie between proximal end 92 and the distal end 91. Post 93 can be used for application of a force directly along axis 100. In this arrangement a handle 102 is mounted on end 103 of arm 98 which provides a gripping location for a surgeon while applying a force to post 93. The required forces can either be applied via post 93 or via handle 102 which allows the surgeon flexibility to select the tool geometry for a particular procedure and choice in the way forces are applied.

Figure 9:
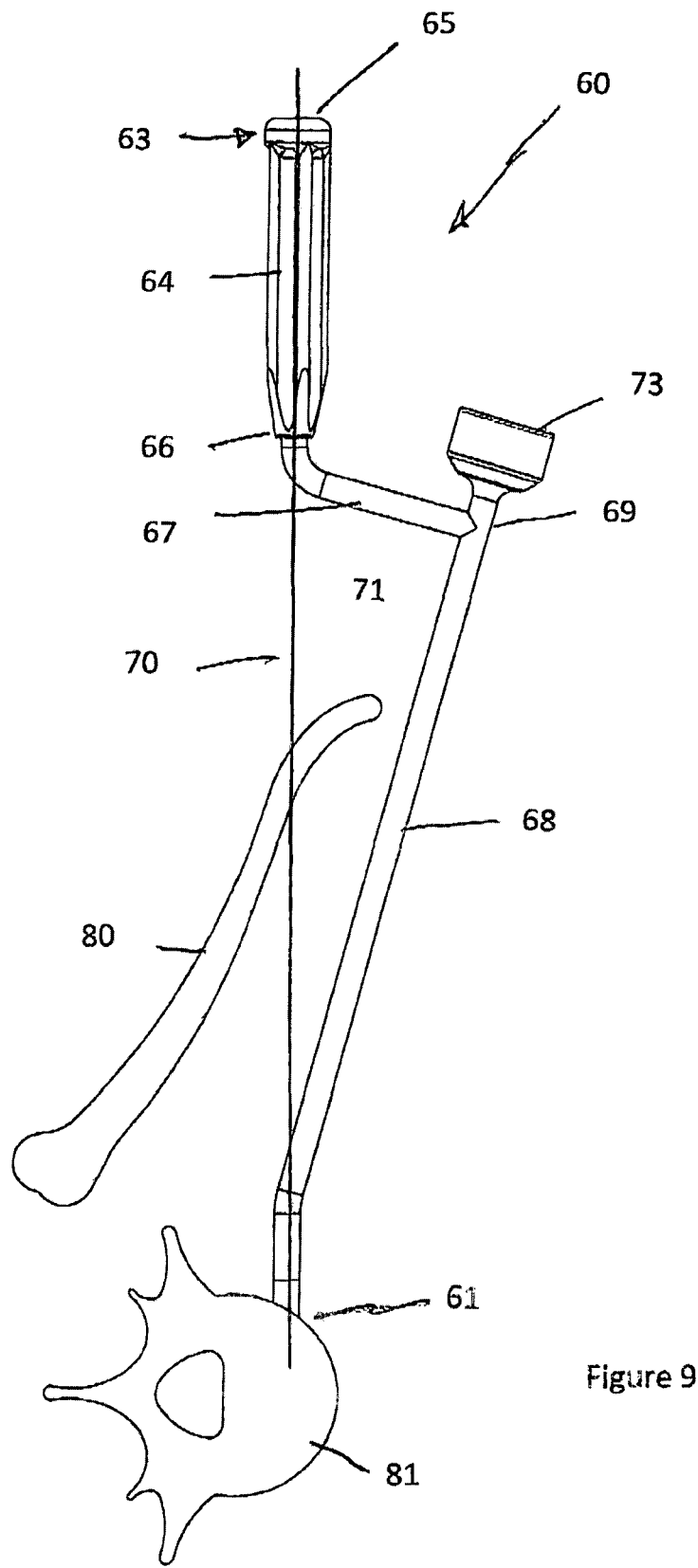
FIG. 9 shows an elevation view of the tool showing the displaced portion avoiding anatomical structures.

FIG. 9 shows with corresponding numbering an elevation view of the tool 60 showing the region 71 allowing arms 67 and 68 to avoid anatomical structure 80. Working formation 61 is shown engaging spinal vertebrae 81. A surgeon working on or around vertebrae 81 can apply a force via handle 64 transmitting an axial or rotational load to distal end 62 (obscured) via longitudinal axis 70 with tool 60 and particularly arms 67 and 68 avoiding anatomical structures soft and hard. Arms 67 and 68 can be substituted with a curved or other shaped member such as but not limited to a U or V shape which can be designed to accommodate a particular form of surgical access required to avoid local anatomy.

Figure 10:
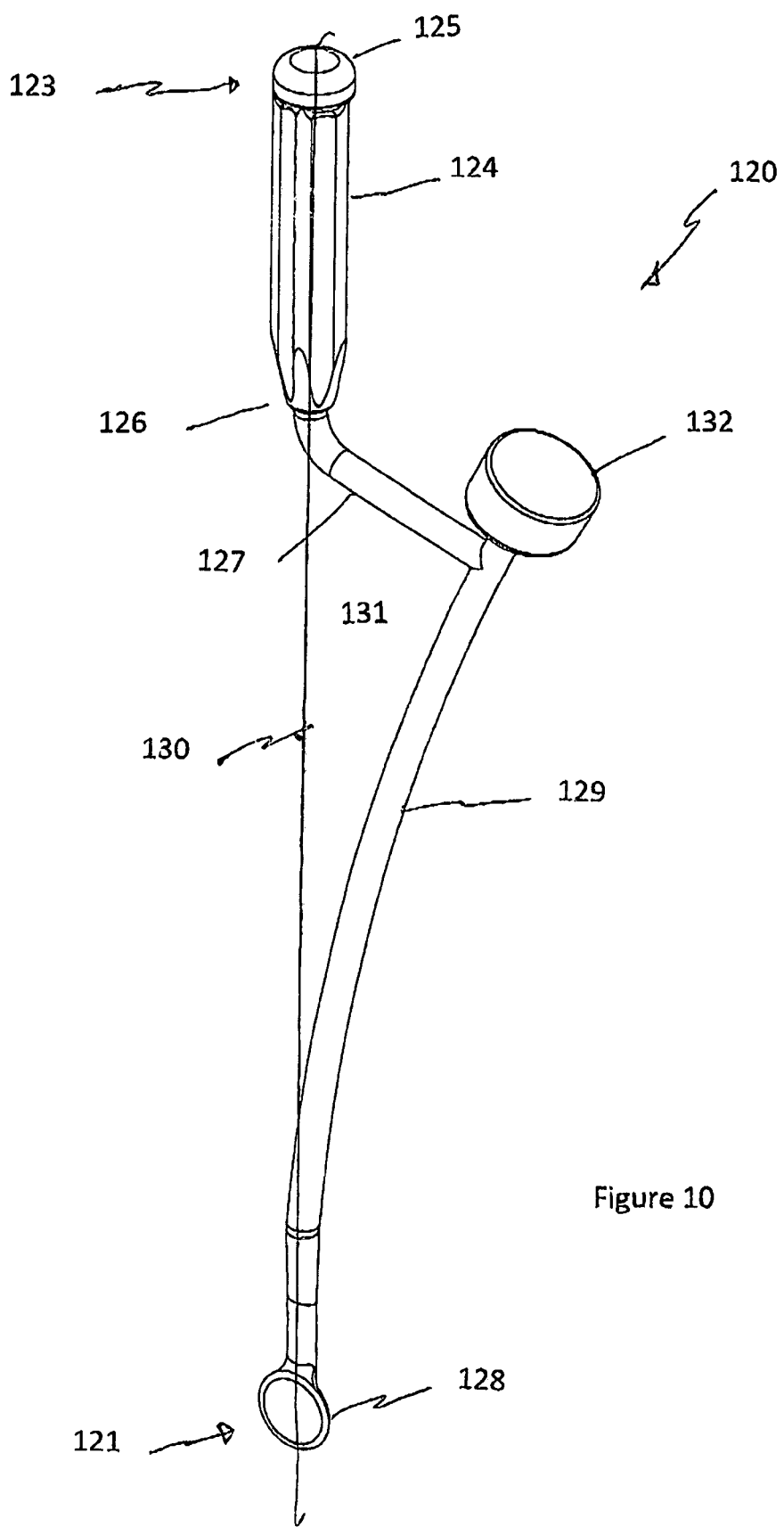
FIG. 10 shows an elevation view of a tool according to an alternative embodiment with an alternative curved displaced portion/offset arm and with spoon working formation.

FIG. 10 shows an elevation view of a tool 120 according to an alternative embodiment with curved displaced portion/offset arm. Tool 120 comprises a distal end 121 and proximal end 122. Proximal end 123 comprises a gripping handle 124 having a free end 125 and terminating at end 126 in joining member 127. Distal end 121 includes a working formation 128. Intermediate working formation 128 and joining member 127 is arm 129 which transfers loads applied to the handle 124 to working formation 128. Tool 120 is characterized in that the handle 124 and working end formation 128 lie along the same longitudinal axis 130. Arm 129 is characterized in that it forms a radiused curve convex in the direction of longitudinal axis 130. Joining member 127 and arm 129 define a region 131 which is offset from the longitudinal axis 132. Region 131 is displaced from the longitudinal axis 130 so that tool 120 can be used to work on a surgical site but at the same time the intermediate displaced region 131 avoids unwanted contact with tissue which lies between the handle end 123 and the working end 122. Extending from end 122 of arm 129 is a platform 132 which can function as a bearing surface for additional applied load such as from a hammer.

Figure 11:
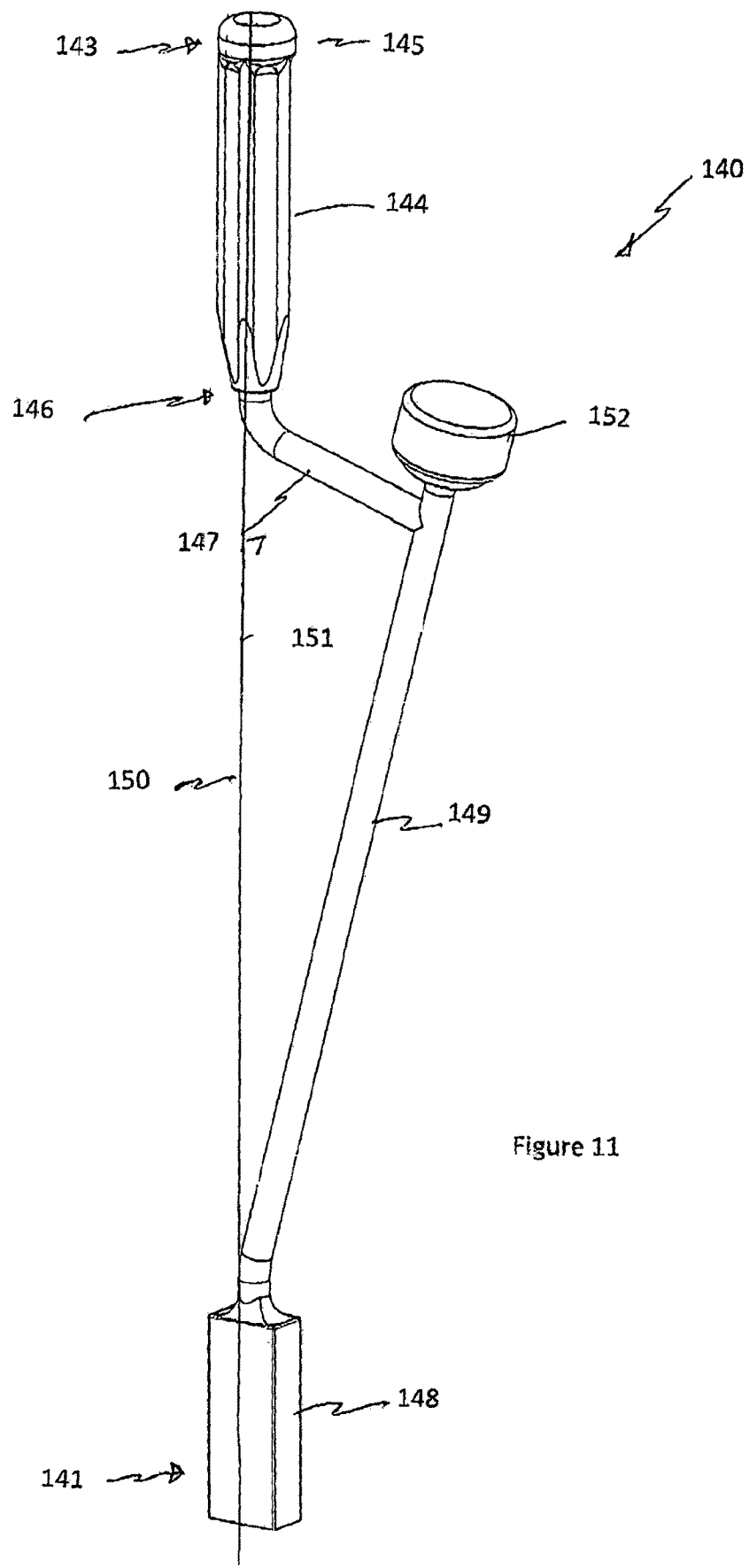
FIG. 11 shows an elevation view of a tool with an alternative working formation in the form of a rectangular block.

FIG. 11 shows an elevation view of a tool 140 with an alternative working formation in the form of a rectangular block, shows an elevation view of a tool 140 according to an alternative embodiment with curved displaced portion/offset arm. Tool 140 comprises a distal end 141 and proximal end 142. Proximal end 143 comprises a gripping handle 144 having a free end 145 and terminating at end 146 in joining member 147. Distal end 141 includes a working formation 148. Working formation 148 is characterized in that it comprises a cubic block which can be selected by the surgeon to accommodate anatomy. Intermediate working formation 148 and joining member 147 is arm 149 which transfers loads applied to the handle 144 to working formation 148. Tool 140 is characterized in that the handle 144 and working end formation 148 lie along the same longitudinal axis 150. Joining member 147 and arm 149 define a region 141 which is offset from the longitudinal axis 142. Region 131 is displaced from the longitudinal axis 142 so that tool 140 can be used to work on a surgical site but at the same time the intermediate displaced region 141 avoids unwanted contact with tissue which lies between the handle end 123 and the working end 142. Extending from end 142 of arm 149 is a platform 133 which can function as a bearing surface for additional applied load such as from a hammer.

Figure 12:
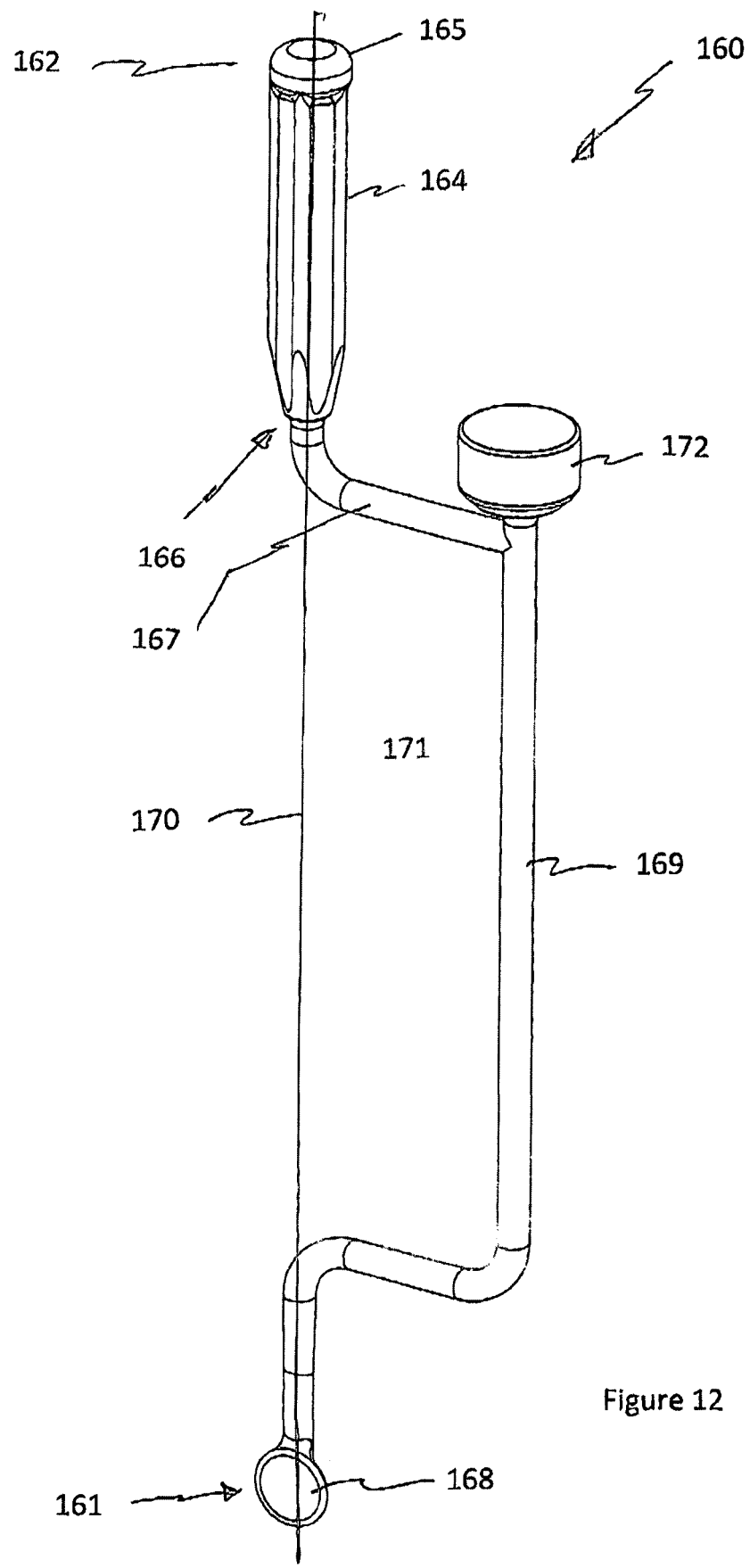
FIG. 12 shows an elevation view of a tool including a displaced portion defining a U shape for avoiding anatomical structures.

FIG. 12 shows an elevation view of a tool 160 including a displaced portion defining a U shape for avoiding anatomical structures. Tool 160 comprises a distal end 161 and proximal end 162. Proximal end 163 comprises a gripping handle 164 having a free end 165 and terminating at end 166 in joining member 167. Distal end 161 includes a working formation 168. Intermediate working formation 168 and joining member 167 is arm 169 which transfers loads applied to the handle 164 to working formation 168. Tool 160 is characterized in that the handle 164 and working end formation 168 lie along the same longitudinal axis 170, Arm 169 is characterized in that it defines an L shape and in combination with joining member 167 forms U shape. This provides an alternative for the surgeon to select as anatomy dictates. Joining member 167 and arm 169 define a region 161 which is offset from the longitudinal axis 162. Region 161 is displaced from the longitudinal axis 162 so that tool 160 can be used to work on a surgical site but at the same time the intermediate displaced region 161 avoids unwanted contact with tissue which lies between the handle end 163 and the working end 162. Extending from end 162 of arm 169 is a platform 163 which can function as a bearing surface for additional applied load such as from a hammer.

Figure 13:
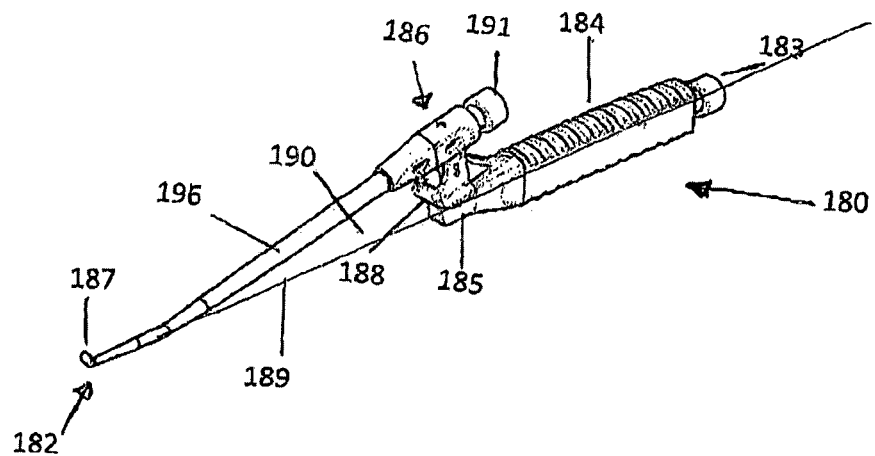
FIG. 13 shows a perspective view of an offset tool according to an alternative embodiment.

FIG. 13 shows a perspective view of an offset tool 180 according to an alternative embodiment. Tool 180 comprises a distal end 182 and proximal end 183. Proximal end 183 comprises a gripping handle 184 terminating at end 185 in joining adapter 186. Distal end 182 includes a working formation 187. Intermediate working formation 187 and joining member 186 is arm 188 which transfers loads applied to the handle 184 to working formation 187. Tool 180 is characterized in that the handle 184 and working end formation 187 lie along the same longitudinal axis 189. Joining adapter 186 and arm 188 define a region 190 which is offset from the longitudinal axis 189, Region 190 is displaced from the longitudinal axis 189 so that tool 180 can be used to work on a surgical site but at the same time the intermediate displaced region 190 avoids unwanted contact with tissue which lies between the handle end 184 and the working distal end 182. Extending from adapter 186 is a member 191 which can function as a bearing surface for additional applied load such as from a hammer and/or which can be depressed to allow release of working attachment 196. Displaced region 190 between the distal end 182 and proximal end 183 enables tool 180 to avoid anatomical structures not involved in an operation. This means that the surgeon had the advantage that while the handle 184 and distal working end 182 are aligned orthogonal to the long axis of the spine and disc space the region defined by joining 186 and arm 188 to avoid anatomy.

Figure 14:
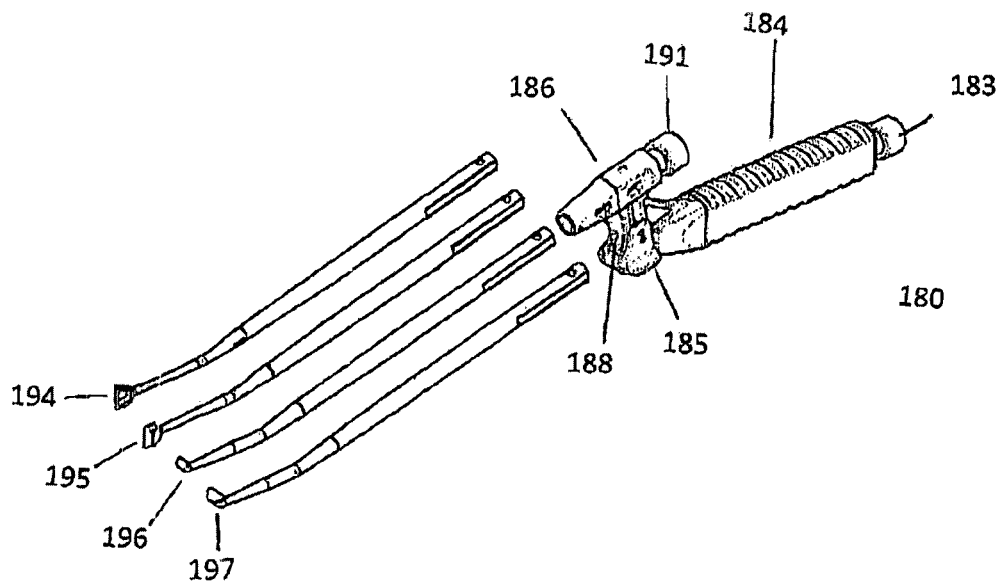
FIG. 14 shows a perspective view of the offset tool of FIG. 13 with a selection of detachable working attachments.

FIG. 14 shows a perspective view of the offset tool 180 of FIG. 13 with a selection of detachable working attachments 194, 195, 196 and 197 which may comprise Cobb elevator, rasp, curettes, distractors, trial implant and implant holder. Other working formations are contemplated depending upon the specific use of the tool 180. Arm 188 and adapter 186 includes a locking mechanism which operates to retain working attachments 194, 195, 196 and 197, The proximal end handle 184 in addition to allowing control of the tool 180 acts as visual indicator of tool alignment so the surgeon, theatre assistants or staff can report if alignment is incorrect. The proximal handle 184 may be used to hold the tool 180 for impaction (e.g., to receive a slap hammer for disc impaction) or help guide the instrument while impaction forces are applied along a straight section of joining member and transferred to the working attachments. Handle 184 is in line with the distal end 182 of the tool which allows surgeons to better judge the alignment of the distal end when it is not directly visible.

Figure 15:
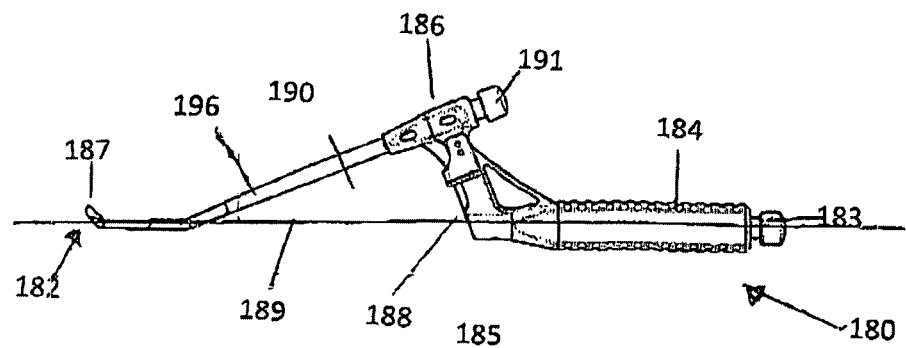
FIG. 15 shows a side elevation view of the offset tool of FIG. 13 with a working attachment.
Figure 16:
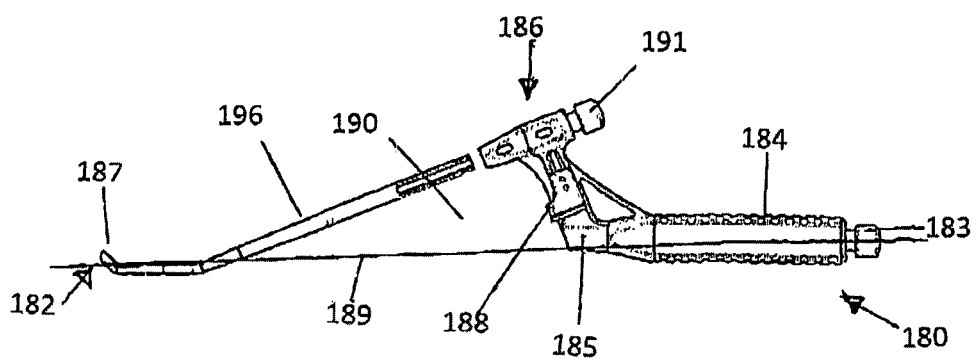
FIG. 16 shows a perspective view of the offset tool of FIG. 15 with the working attachment detached.
Figure 17:
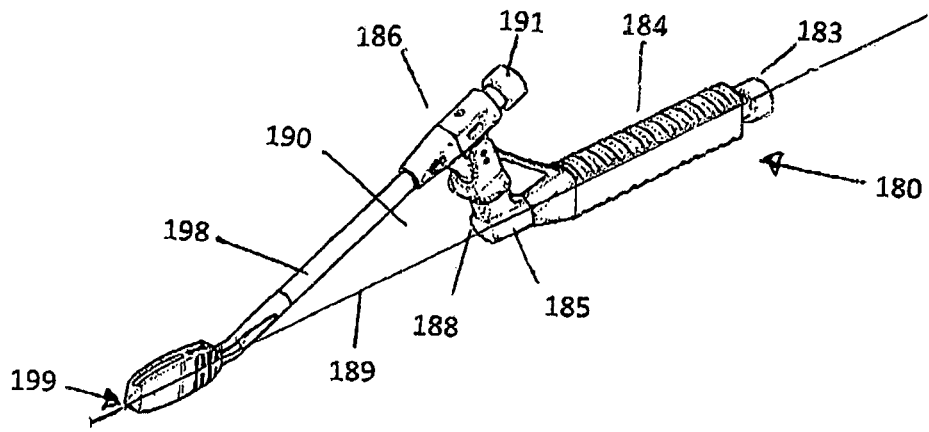
FIG. 17 shows a perspective view of the offset tool of FIG. 13 with an alternative working attachment.
Figure 18:
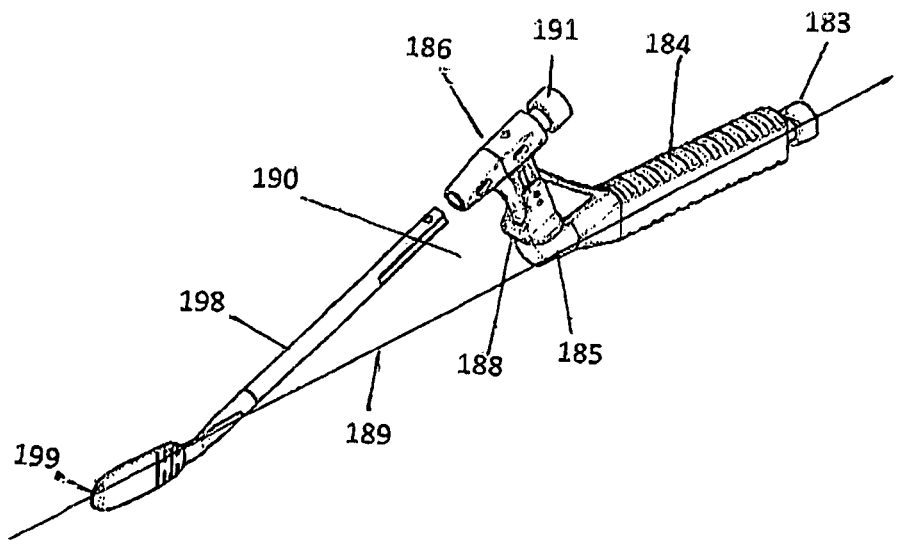
FIG. 18 shows the offset tool of FIG. 17 with working attachment detached.
Figure 19:
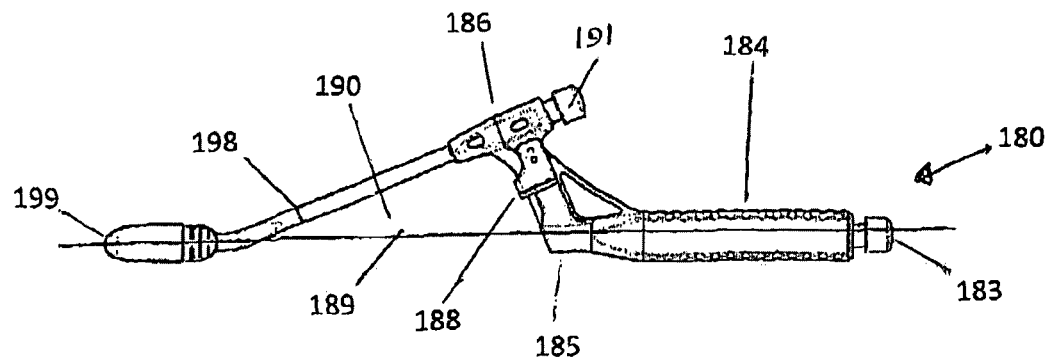
FIG. 19 shows a side elevation view of the offset tool of FIG. 13 with an alternative working attachment.
Figure 20:
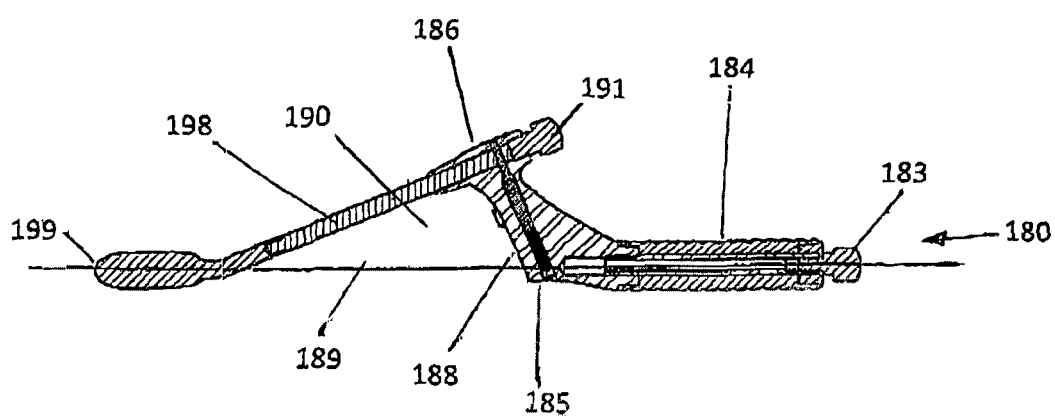
FIG. 20 shows a long sectional view of the offset tool of FIG. 19 with the working attachment attached.
Figure 21:
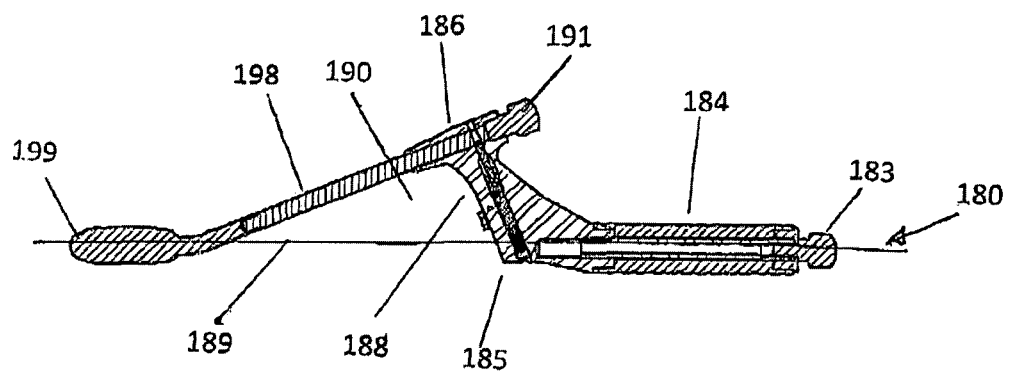
FIG. 21 shows a side elevation view of the offset tool of FIG. 20 with an alternative working attachment.
Figure 22:
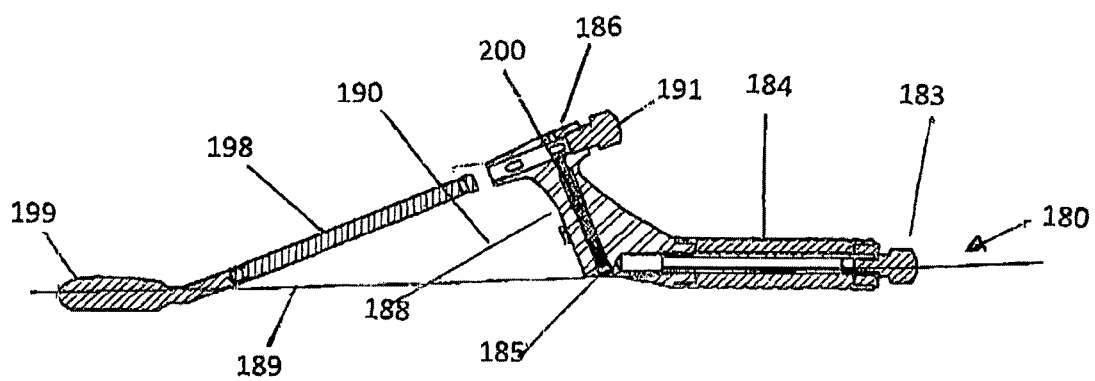
FIG. 22 shows a long sectional view of the offset tool of FIG. 20 with the working attachment detached.
Figure 23:
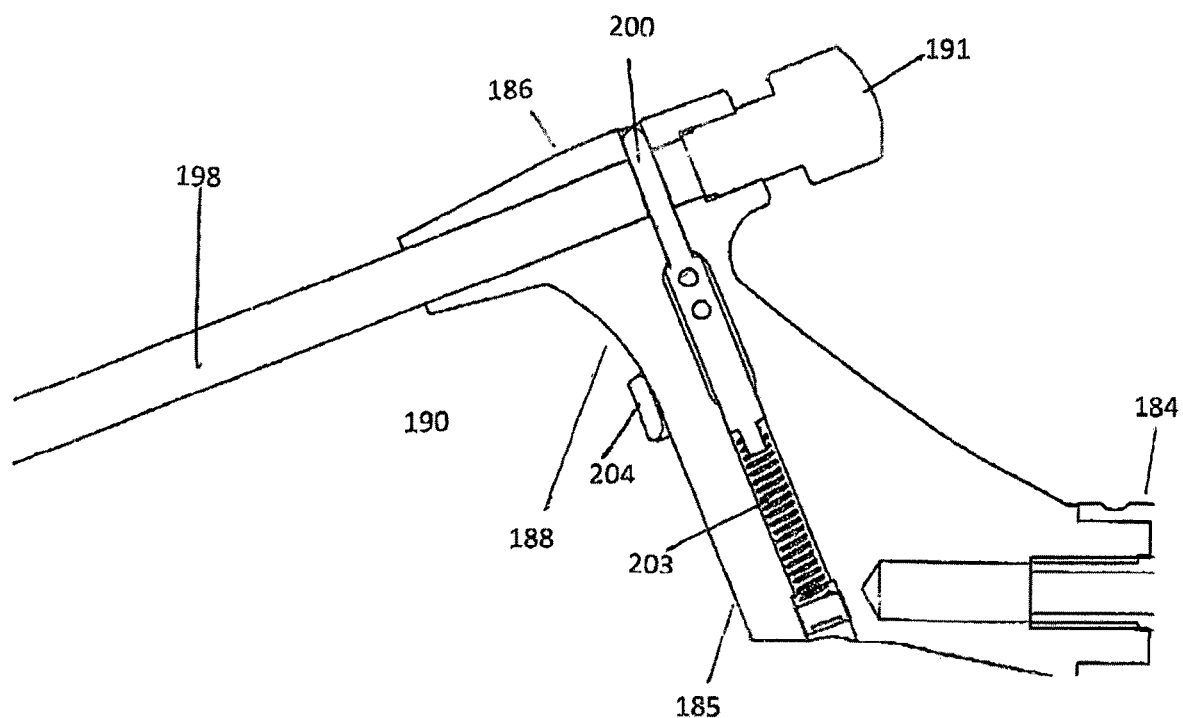
FIG. 23 shows an enlarged view of a part long sectional view of the locking assembly which retains, the working attachment.
Figure 24:
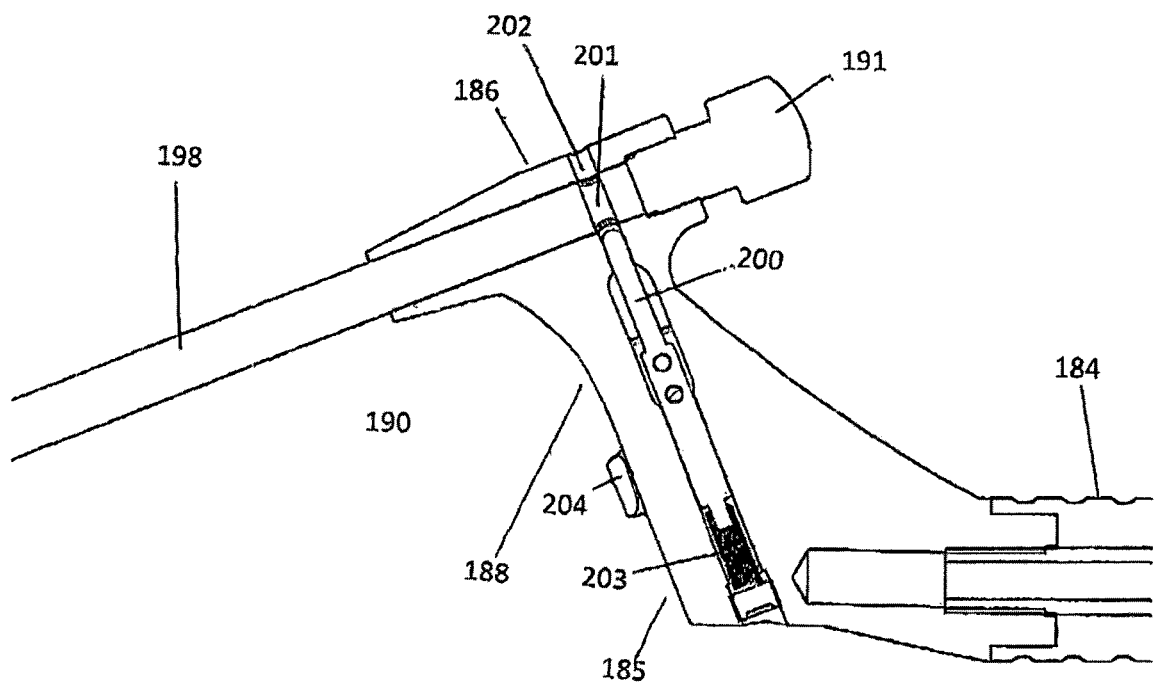
FIG. 24 shows the part long sectional view of FIG. 23 with the locking mechanism retracted to enable release the working implement.
Figure 25:
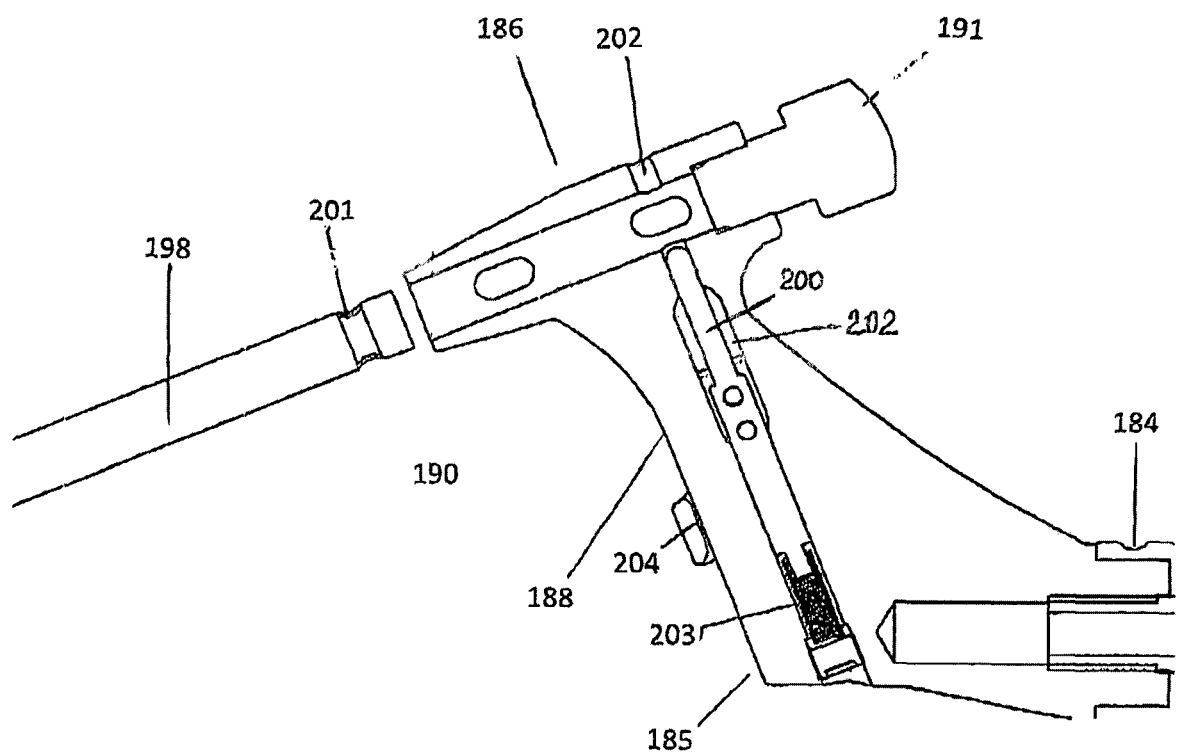
FIG. 25 shows the part long sectional view of FIG. 24 with the locking mechanism retracted and the working implement released.

FIG. 15 shows with corresponding numbering a side elevation view of the offset tool 180 of FIG. 13 with the working attachment 196. FIG. 16 shows an elevation of the offset tool 180 of FIG. 15 with the working attachment 196 detached from adaptor 186, FIG. 17 shows with corresponding numbering a perspective view of the offset tool 180 of FIG. 13 with an alternative working attachment 198 attached to adaptor 186. FIG. 18 shows the offset tool of FIG. 17 with working attachment 198 detached from adaptor 186. As with the embodiments of FIGS. 15 and 16 longitudinal axis 189 passes through handle 184 and working end 199 of attachment 198. FIG. 19 shows a side elevation view of the offset tool 180 of FIG. 13 with an alternative working attachment 198 retained by adaptor 186. FIG. 20 shows a long sectional view through the offset tool 180 of FIG. 19 with the working attachment attached. This view shows the components of the locking assembly which allows selective attachment and detachment of working attachment 198. Attachment 198 is shown in FIG. 20 locked in position in adaptor 186. In the locked position retaining pin 200 engages working member 198 to selectively retain member 198 in locked position. FIG. 21 shows with corresponding numbering, a side elevation view of the offset tool 180 of FIG. 20 with retaining pin 200 retracted away from working attachment 198. FIG. 22 shows a long sectional view of the offset tool of FIG. 20 with the working attachment 198 detached. FIGS. 23, 24 and 25 respectively show enlarged views of the locking mechanism of FIGS. 20, 21 and 22.

FIG. 23 shows an enlarged view of a part long sectional view of the locking assembly which retains the working attachment 198. In the embodiment of FIG. 23 the working attachment 198 is shown locked in position by locking pin 200 which extends into recess 201 (see FIG. 24) of attachment 198. Retaining pin 200 travels in passage 202 and is capable of extension and retraction under the action of bias spring 203. In FIG. 23 biasing spring 203 is fully extended such that it urges locking pin 200 into engagement with recess 201 working attachment 198. Associated with locking pin 200 is a finger operated latch 204 which allows a user to effect selective manual retraction and extension of locking pin 200 for respective release and engagement of working attachment 198.

FIG. 24 shows with corresponding numbering the part long sectional view of FIG. 23 with the locking pin 200 retracted clear of recess 201 to enable release the working implement 198. To eject the working attachment 198 the user slides latch 204 against biasing spring 203. This results in retraction of locking pin 200 away from working attachment 198. FIG. 25 shows the part long sectional view of FIG. 24 with the locking pin fully retracted and the working implement 198 released.

It will be appreciated by persons skilled in the art that numerous variations may be made to the tools described above such as knurling the handle for improved grip, providing distal ends that are different from shaft in one or more planes, the provision of compound angled instruments (i.e. with compound angled working end forming an angle with shaft that is in two or more planes; likewise long axis of handle is different in two planes but still has same long axis as working end). Particularly for use at L5S1 to allow use from a position that is both superior and anterior to a disc space. Further variations include the use at the working end of a Cobb elevator, Curretes, dissectors, rasps, shavers, trial implant and implants holders and implants and other instruments used for such surgery, Although the tool is preferred for use in spinal surgery including, disc space for disc removal, endplate preparation, bone removal or vertebral body removal or distraction, it may potentially have other applications in blind alignment of proximal and distal ends. Such instruments may be made with angles that allow approach to the disc space from a superior direction as per the aforesaid existing Nuvasive XLIF instruments but unlike the XLIF instruments the handle of a tool according to the present invention has a co linear axis with the distal end section.

Such instruments may be manufactured with angles that allow an approach to the disc space from an anterior direction for use in anterolateral surgery. In an alternative embodiment the tool has aligned ends with co linear axes and intermediate offset region is used in Thoracic spine surgery where approach between the ribs is not perfectly aligned with the disc space, e.g. crank instruments. Use of a tool made in accordance with the present invention is adapted for use in endoscopic surgery is envisaged.

According to one embodiment the intermediate offset shaft region of the tool comprises straight, curved or angled sections as required depending upon required force transmission path. In a further embodiment the working end includes a releasing mechanism to hold trials or implants or interchangeable/rotatable working ends. This arrangement reduces the number of tools required in the inventory. In another embodiment the offset shaft region includes depth indicators to enable a surgeon to judge distances related to anatomy. The tool may also include an intermediate offset shaft which be curved or angled. Ends may be aligned to allow transmission of axial impact from the proximal end to the working end and the intermediate section is arranged to control unwanted moment or rotational effects.

Although the figures show the tool according to various embodiments, it will be appreciated that the geometry of the tool can be altered to suit anatomical requirements such as but not limited to changing the angle of the offset regions, changing the distance of the most distant part of the offset region form the longitudinal axis, altering the shapes defined by the offsets using angled, rectangular or square offsets. For certain surgical procedures according to one embodiment, an offset angle greater than 15 degrees can be defined by the boundary of the offset region used extending up to 45 degrees. The angle and displacement can therefore be adapted to suit avoidance of anatomy during all surgical approaches.

It will be recognized by persons skilled in the art that numerous variations and modifications may be made to the invention as broadly described herein without departing from the overall scope of the invention.

What is claimed is:

1. A surgical tool for use in gaining access to a spine, the surgical tool comprising:
 a handle having a longitudinal axis;
 a post having a free end and a longitudinal axis, wherein said longitudinal axis of the post intersects with the longitudinal axis of the handle;
 a joining member and a single unitary arm, said joining member having a first end connected to the post and a second end connected to the arm, the joining member and the arm being offset from the longitudinal axis of the post to avoid anatomical structures during use of a working formation, wherein a first portion of the arm comprising a length that is offset from the longitudinal axis of the post and a second portion of the arm comprising a length that lies on the longitudinal axis of the post, the length of the first portion of the arm being greater than the length of the second portion of the arm, wherein the arm lies along the longitudinal axis of the handle; and wherein the working formation is connected to the arm such that the working formation lies along the longitudinal axis of the post.

2. The surgical tool of claim 1, wherein the post terminates at the joining member.

3. The surgical tool of claim 1, wherein the handle is connected to the arm.

4. The surgical tool of claim 1, wherein the working formation is a dissector.

5. The surgical tool of claim 1, wherein the working formation is a rasp.

6. The surgical tool of claim 1, wherein the working formation is a shaver.

7. The surgical tool of claim 1, wherein the working formation is an implant holder.

8. The surgical tool of claim 1, wherein the longitudinal axis of post is not coaxial with the longitudinal axis of the handle.

9. The surgical tool of claim 1,
wherein the handle is the only handle;
wherein the post is the only post;
wherein the joining member is the only joining member;
wherein the single unitary arm is the only single unitary arm; and
wherein the working formation is the only working formation.

10. A surgical tool for use in gaining access to a spine, the surgical tool comprising:
a handle having a longitudinal axis;
a post having a free end and a longitudinal axis, wherein said longitudinal axis of the post intersects with the longitudinal axis of the handle;
a joining member and a single unitary arm, said joining member having a first end connected to the post and a second end connected to the arm, the joining member and the arm defining a region that is offset from the longitudinal axis of the post to avoid anatomical structures during use of a working formation, wherein the arm lies along the longitudinal axis of the handle; and
said working formation being connected to the arm such that the working formation lies along the longitudinal axis of the post,
wherein the handle is the only handle;
wherein the post is the only post;
wherein the joining member is the only joining member;
wherein the single unitary arm is the only single unitary arm; and
wherein the working formation is the only working formation.

* * * * *